US006392022B1

(12) United States Patent
Kato et al.

(10) Patent No.: US 6,392,022 B1
(45) Date of Patent: May 21, 2002

(54) GENE ORIGINATING IN HUMAN CHONDROCYTE

(75) Inventors: Yukio Kato, Hiroshima; Takeshi Kawamoto, Yamaguchi, both of (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/462,624

(22) PCT Filed: Jul. 10, 1998

(86) PCT No.: PCT/JP98/03106

§ 371 Date: Jan. 11, 2000

§ 102(e) Date: Jan. 11, 2000

(87) PCT Pub. No.: WO99/02677

PCT Pub. Date: Jan. 21, 1999

(30) Foreign Application Priority Data

Jul. 11, 1997 (JP) ............................................. 9-202227

(51) Int. Cl.$^7$ ......................... C07H 17/00; C07K 14/00
(52) U.S. Cl. ........................ 536/23.1; 530/350; 530/300
(58) Field of Search ................................. 530/350, 300; 536/23.1

(56) References Cited

U.S. PATENT DOCUMENTS 5,882,894 A * 3/1999 Smith et al. ................ 435/69.1

FOREIGN PATENT DOCUMENTS

WO    WO 96/39427    12/1996

OTHER PUBLICATIONS

Shen et al. 1997. Biochem. Biophys. Res. Commun. 236:294–298.*

Ming Shen et al., "Molecular Characterization of the Novel Basic Helix–Loop–Helix Protein DEC1 Expressed in Differentiated Human Embryo Chondrocytes", Biochemical and Biophysical Research Communications 236, 1997, pp. 294–298.

Yukio Kato et al., "Terminal Differentiation and Calcification in Rabbit Chondrocyte Cultures Grown in Centrifuge Tubes: Regulation by Transforming Growth Factor β and Serum Factors", Proc. Natl. Acad. Sci. USA, vol. 85, Dec. 1988, pp. 9552–9556.

B. W. Oakes et al., "An Ultrastructural and Biochemical Study of High Density Primary Cultures of Embryonic Chick Chondrocytes", J. Embroyol. exp. Morph., vol. 38, 1977, pp. 239–263.

Paul D. Benya et al., "Dedifferentiated Chondrocytes Reexpress the Differentiated Collagen Phenotype When Cultured in Agarose Gels", Cell, vol. 30, Aug. 1982, pp. 215–224.

Yoshiki Sasai et al., "Two Mammalian Helix–Loop–Helix Factors Structurally Related to Drosophila Hairy and Enhancer of Split", Genes & Development vol. 6 1992, pp. 2620–2634.

Makoto Ishibashi et al., "Molecular Characterization of HES–2, a Mammalian Helix–Loop–Helix Factor Structurally Related to Drosophila Hairy and Enhancer of Split", Eur. J. Biochem 215, 1993, pp. 645–652.

Chihiro Akazawa et al., "Molecular Characterization of a Rat Negative Regulator With a Basic Helix–Loop–Helix Structure Predominantly Expressed in the Developing Nervous System", The Journal of Biological Chemistry 1992, pp. 21879–21885.

Shunji Ohsako et al., "Hairy Function as a DNA–Binding Helix–Loop–Helix Repressor of Drosophila Sensory Organ Formation", Genes & Development 1994 vol. 8, pp. 2743–2755.

Stephanie R. Dawson et al., "Specificity for the Hairy/Enhancer of Split Basic Helix–Loop–Helix (bHLH) Proteins Maps Outside the bHLH Domain and Suggests Two Separable Modes of Transcriptional Repression," Molecular and Cellular Biology, Dec. 1995, pp. 6923–6931.

Yuh Nung Jan et al., "HLH Proteins, Fly Neurogenesis, and Vertebrate Myogenesis", Cell, vol. 75, Dec. 3, 1993, pp. 827–830.

Y. Shimomura et al., "Osteogenesis by Chondrocytes from Growth Cartilage of Rat Rib", Calcif. Tiss. Res. 19, 1975, pp. 175–187.

Georgeann Smale et al., "RNA Isolation from Cartilage Using Density Gradient Centrifugation in Cesium Trifluoroacetate: An RNA Preparation Technique Effective in the Presence of High Proteoglycan Content", Analytical Biochemistry 203, 1992, pp. 352–356.

* cited by examiner

*Primary Examiner*—Karen Cochrane Carlson
(74) *Attorney, Agent, or Firm*—Morgan, Lewis & Bockius LLP

(57) ABSTRACT

This invention provides a gene specifically expressed in differentiated human chondrocytes. By culturing the chondrocytes in the presence of dibutyryl cAMP, the chondrocytes are cultured in a differentiated state and any gene is searched for which has a distinction in expression between differentiated chrondrocytes and dedifferentiated chrondrocytes. This allows the gene specifically expressed in the former to be obtained.

3 Claims, 8 Drawing Sheets

|         | BASIC      | HELIX 1                    | LOOP                    | HELIX 2                      |
|---------|------------|----------------------------|-------------------------|------------------------------|
| DEC1    | ETYKLPHRL  IEKKRRDRINECIAQLKDL- | LPEHLKLTTLGH- | -LEKAVVLELTLKHVKALT |
| HES1    | EHRKSSKPIMEKRRRARINESLSQLKTLIL- | DALKKDSSRHS | KLEKADILEMTVKHLRNLQ |
| HES2    | ELRKSLKPL  LEKRRRARINESLSQLKGLVLPL- | LGAETSRYS | KLEKADILEMTVRFLRE-Q |
| HES3    | MEKKRRARINLSLEQLRSL-L- | ERHYSHQIRKRKL | EKADILELSVKKYVRSLQ |
| HES5    | EKNRLRKPVVEKMRRDRINSSIEQLKLL-L- | EQEFARHQPNS | KLEMAVSYLKISK |
| Hairy   | SDRRSNKPIMEKRRRARINNCLNELKTLIL- | DATKKDPARH | SKLEKADILEKTVKHLQELQ |
| E(spl) m7 | QYRKVMKPL  LERKRRARINKCLDELKDLMA- | ECVAQTGDA- | -KFEKADILEVIVQHLRKLK |
| MyoD    | ADRRKAATMRERRRLSKVNEAFETLKRCTS- | SNPNQR---- | -LPKVEILRNAIRYIEGLQ |

*FIG. 1*

SEQUENCE LISTING

```
<160> NUMBER OF SEQ ID NOS:  3

<210> SEQ ID NO 1
<211> LENGTH: 2948
<212> TYPE: DNA
<213> ORGANISM: Homo sapiens
<220> FEATURE:
<221> NAME/KEY: CDS
<222> LOCATION: (207)..(1442)
<223> OTHER INFORMATION: Transcription factor DEC1

<400> SEQUENCE: 1
attacgaact ggacaccggg ccatgcacgc ccccaactga agctgcatct c aaagccgaa      60 gattccagca gcccagggga tttcaaagag ctcagactca gaggaacatc t gcggagaga     120 cccccgaagc cctctccagg gcagtcctca tccagacgct ccgctagtgc a gacaggagc    180 gcgcagtggc cccggctcgc cgcgcc atg gag cgg atc ccc agc gcg caa cca      233
                              Met Glu Arg Ile Pro Ser Ala Gln Pro
                                1               5 ccc ccc gcc tgc ctg ccc aaa gca ccg gga c tg gag cac gga gac cta      281
Pro Pro Ala Cys Leu Pro Lys Ala Pro Gly L eu Glu His Gly Asp Leu
 10              15                  20                  25 cca ggg atg tac cct gcc cac atg tac caa g tg tac aag tca aga cgg      329
Pro Gly Met Tyr Pro Ala His Met Tyr Gln V al Tyr Lys Ser Arg Arg
             30                  35                  40
```

-continued

```
gga ata aag cgg agc gag gac agc aag gag a cc tac aaa ttg ccg cac     377
Gly Ile Lys Arg Ser Glu Asp Ser Lys Glu T hr Tyr Lys Leu Pro His
            45                  50                  55 cgg ctc atc gag aaa aag aga cgt gac cgg a tt aac gag tgc atc gcc     425
Arg Leu Ile Glu Lys Lys Arg Asp Arg I le Asn Glu Cys Ile Ala
        60                  65                  70 cag ctg aag gat ctc cta ccc gaa cat ctc a aa ctt aca act ttg ggt     473
Gln Leu Lys Asp Leu Leu Pro Glu His Leu L ys Leu Thr Thr Leu Gly
    75                  80                  85 cac ttg gaa aaa gca gtg gtt ctt gaa ctt a cc ttg aag cat gtg aaa     521
His Leu Glu Lys Ala Val Val Leu Glu Leu T hr Leu Lys His Val Lys
 90                  95                 100                 105 gca cta aca aac cta att gat cag cag cag c ag aaa atc att gcc ctg     569
Ala Leu Thr Asn Leu Ile Asp Gln Gln Gln G ln Lys Ile Ile Ala Leu
            110                 115                 120 cag agt ggt tta caa gct ggt gag ctg tca g gg aga aat gtc gaa aca     617
Gln Ser Gly Leu Gln Ala Gly Glu Leu Ser G ly Arg Asn Val Glu Thr
        125                 130                 135 ggt caa gag atg ttc tgc tca ggt ttc cag a ca tgt gcc cgg gag gtg     665
Gly Gln Glu Met Phe Cys Ser Gly Phe Gln T hr Cys Ala Arg Glu Val
    140                 145                 150 ctt cag tat ctg gcc aag cac gag aac act c gg gac ctg aag tct tcg     713
Leu Gln Tyr Leu Ala Lys His Glu Asn Thr A rg Asp Leu Lys Ser Ser
155                 160                 165 cag ctt gtc acc cac ctc cac cgg gtg gtc t cg gag ctg ctg cag ggt     761
Gln Leu Val Thr His Leu His Arg Val Val S er Glu Leu Leu Gln Gly
170                 175                 180                 185 ggt acc tcc agg aag cca tca gac cca gct c cc aaa gtg atg gac ttc     809
Gly Thr Ser Arg Lys Pro Ser Asp Pro Ala P ro Lys Val Met Asp Phe
            190                 195                 200 aag gaa aaa ccc agc tct ccg gcc aaa ggt t cg gaa ggt cct ggg aaa     857
Lys Glu Lys Pro Ser Ser Pro Ala Lys Gly S er Glu Gly Pro Gly Lys
        205                 210                 215 aac tgc gtg cca gtc atc cag cgg act ttc g ct cac tcg agt ggg gag     905
Asn Cys Val Pro Val Ile Gln Arg Thr Phe A la His Ser Ser Gly Glu
    220                 225                 230 cag agc ggc agc gac acg gac aca gac agt g gc tat gga gga gaa tcg     953
Gln Ser Gly Ser Asp Thr Asp Thr Asp Ser G ly Tyr Gly Gly Glu Ser
235                 240                 245 gag aag ggc gac ttg cgc agt gag cag ccg t gc ttc aaa agt gac cac    1001
Glu Lys Gly Asp Leu Arg Ser Glu Gln Pro C ys Phe Lys Ser Asp His
250                 255                 260                 265 gga cgc agg ttc acg atg gga gaa agg atc g gc gca att aag caa gag    1049
Gly Arg Arg Phe Thr Met Gly Glu Arg Ile G ly Ala Ile Lys Gln Glu
            270                 275                 280 tcc gaa gaa ccc ccc aca aaa aag aac cgg a tg cag ctt tcg gat gat    1097
Ser Glu Glu Pro Pro Thr Lys Lys Asn Arg M et Gln Leu Ser Asp Asp
        285                 290                 295 gaa ggc cat ttc act agc agt gac ctg atc a gc tcc ccg ttc ctg ggc    1145
Glu Gly His Phe Thr Ser Ser Asp Leu Ile S er Ser Pro Phe Leu Gly
    300                 305                 310 cca cac cca cac cag cct cct ttc tgc ctg c cc ttc tac ctg atc cca    1193
Pro His Pro His Gln Pro Pro Phe Cys Leu P ro Phe Tyr Leu Ile Pro
315                 320                 325 cct tca gcg act gcc tac ctg ccc atg ctg g ag aag tgc tgg tat ccc    1241
Pro Ser Ala Thr Ala Tyr Leu Pro Met Leu G lu Lys Cys Trp Tyr Pro
330                 335                 340                 345 acc tca gtg cca gtg cta tac cca ggc ctc a ac gcc tct gcc gca gcc    1289
Thr Ser Val Pro Val Leu Tyr Pro Gly Leu A sn Ala Ser Ala Ala Ala
            350                 355                 360
```

```
ctc tct agc ttc atg aac cca gac aag atc t cg gct ccc ttg ctc atg      1337
Leu Ser Ser Phe Met Asn Pro Asp Lys Ile S er Ala Pro Leu Leu Met
            365                 370                 375 ccc cag aga ctc cct tct ccc ttg cca gct c at ccg tcc gtc gac tct      1385
Pro Gln Arg Leu Pro Ser Pro Leu Pro Ala H is Pro Ser Val Asp Ser
            380                 385                 390 tct gtc ttg ctc caa gct ctg aag cca atc c cc cct tta aac tta gaa      1433
Ser Val Leu Leu Gln Ala Leu Lys Pro Ile P ro Pro Leu Asn Leu Glu
            395                 400                 405 acc aaa gac taaactctct aggggatcct gctgctttgc tttccttc ct              1482
Thr Lys Asp
410 cgctacttcc taaaaagcaa caaaaaagtt tttgtgaatg ctgcaagatt g ttgcattgt    1542
gtatactgag ataatctgag gcatggagag cagattcagg gtgtgtgtgt g tgtgtgtgt    1602
gtgtgtgtgt atgtgcgtgt gcgtgcacat gtgtgcctgc gtgttggtat a ggactttaa    1662
agctcctttt ggcataggga agtcacgaag gattgcttga catcaggaga c ttgggggggg   1722
attgtagcag acgtctgggc ttttccccac ccagagaata gccccttcg a tacacatca     1782
gctggatttt caaaagcttc aaagtcttgg tctgtgagtc actcttcagt t tgggagctg    1842
ggtctgtggc tttgatcaga aggtactttc aaaagagggc tttccaggc t cagctccca    1902
accagctgtt aggaccccac ccttttgcct ttattgtcga cgtgactcac c agacgtcgg    1962
ggagagagag cagtcagacc gagctttctg ctaacatggg gaggtagcag g cactggcat   2022
agcacggtag tggtttgggg aggtttccgc aggtctgctc cccaccctg c ctcggaaga     2082
ataaagagaa tgtagttccc tactcaggct tcgtagtga ttagcttact a aggaactga    2142
aaatgggccc cttgtacaag ctgagctgcc ccggagggag ggaggagttc c ctgggcttc    2202
tggcacctgt ttctaggcct aaccattagt acttactgtg cagggaacca a accaaggtc    2262
tgagaaatgc ggacacccg agcgagcacc ccaaagtgca caaagctgag t aaaaagctg    2322
ccccccttcaa acagaactag actcagtttt caattccatc ctaaaactcc t tttaaccaa   2382
gcttagcttc tcaaaggcct aaccaagcct tggcaccgcc agatcctttc t gtaggctaa    2442
ttcctcttgc ccaacggcat atggagtgtc cttattgcta aaaaggattc c gtctccttc   2502
aaagaagttt tattttggt ccagagtact tgttttcccg atgtgtccag c cagctccgc     2562
agcagctttt caagatgcac tatgcctgat tgctgatcgt gttttaactt t ttcttttcc   2622
tgtttttatt ttggtattaa gtcgttgcct ttatttgtaa agctgttata a atatatatt   2682
atataaatat attaaaaagg aaaatgtttc agatgtttat ttgtataatt a cttgattca    2742
cacagtgaga aaaatgaat gtattcctgt ttttgaagag aagaataatt t ttttttctc   2802
tagggagagg tacagtgttt atattttgga gccttcctga aggtgtaaaa t tgtaaatat    2862
ttttatctat gagtaaatgt taagtagttg ttttaaaata cttaataaaa t aattctttt   2922
cctgtggaag aaaaaaaaaa aaaaaa                                          2948

<210> SEQ ID NO 2
<211> LENGTH: 412
<212> TYPE: PRT
<213> ORGANISM: Homo sapiens

<400> SEQUENCE: 2

Met Glu Arg Ile Pro Ser Ala Gln Pro Pro P ro Ala Cys Leu Pro Lys
  1               5                  10                  15

Ala Pro Gly Leu Glu His Gly Asp Leu Pro G ly Met Tyr Pro Ala His
```

```
                   20                  25                  30
Met Tyr Gln Val Tyr Lys Ser Arg Arg Gly I le Lys Arg Ser Glu Asp
                35                  40                  45

Ser Lys Glu Thr Tyr Lys Leu Pro His Arg L eu Ile Glu Lys Lys Arg
 50                  55                  60

Arg Asp Arg Ile Asn Glu Cys Ile Ala Gln L eu Lys Asp Leu Leu Pro
 65                  70                  75                  80

Glu His Leu Lys Leu Thr Thr Leu Gly His L eu Glu Lys Ala Val Val
                85                  90                  95

Leu Glu Leu Thr Leu Lys His Val Lys Ala L eu Thr Asn Leu Ile Asp
               100                 105                 110

Gln Gln Gln Gln Lys Ile Ile Ala Leu Gln S er Gly Leu Gln Ala Gly
               115                 120                 125

Glu Leu Ser Gly Arg Asn Val Glu Thr Gly G ln Glu Met Phe Cys Ser
               130                 135                 140

Gly Phe Gln Thr Cys Ala Arg Glu Val Leu G ln Tyr Leu Ala Lys His
145                 150                 155                 160

Glu Asn Thr Arg Asp Leu Lys Ser Ser Gln L eu Val Thr His Leu His
               165                 170                 175

Arg Val Val Ser Glu Leu Leu Gln Gly Gly T hr Ser Arg Lys Pro Ser
               180                 185                 190

Asp Pro Ala Pro Lys Val Met Asp Phe Lys G lu Lys Pro Ser Ser Pro
               195                 200                 205

Ala Lys Gly Ser Glu Gly Pro Gly Lys Asn C ys Val Pro Val Ile Gln
               210                 215                 220

Arg Thr Phe Ala His Ser Ser Gly Glu Gln S er Gly Ser Asp Thr Asp
225                 230                 235                 240

Thr Asp Ser Gly Tyr Gly Gly Glu Ser Glu L ys Gly Asp Leu Arg Ser
               245                 250                 255

Glu Gln Pro Cys Phe Lys Ser Asp His Gly A rg Arg Phe Thr Met Gly
               260                 265                 270

Glu Arg Ile Gly Ala Ile Lys Gln Glu Ser G lu Glu Pro Pro Thr Lys
               275                 280                 285

Lys Asn Arg Met Gln Leu Ser Asp Asp Glu G ly His Phe Thr Ser Ser
               290                 295                 300

Asp Leu Ile Ser Ser Pro Phe Leu Gly Pro H is Pro His Gln Pro Pro
305                 310                 315                 320

Phe Cys Leu Pro Phe Tyr Leu Ile Pro Pro S er Ala Thr Ala Tyr Leu
               325                 330                 335

Pro Met Leu Glu Lys Cys Trp Tyr Pro Thr S er Val Pro Val Leu Tyr
               340                 345                 350

Pro Gly Leu Asn Ala Ser Ala Ala Ala Leu S er Ser Phe Met Asn Pro
               355                 360                 365

Asp Lys Ile Ser Ala Pro Leu Leu Met Pro G ln Arg Leu Pro Ser Pro
370                 375                 380

Leu Pro Ala His Pro Ser Val Asp Ser Ser V al Leu Leu Gln Ala Leu
385                 390                 395                 400

Lys Pro Ile Pro Pro Leu Asn Leu Glu Thr L ys Asp
               405                 410

<210> SEQ ID NO 3
<211> LENGTH: 4
<212> TYPE: PRT
<213> ORGANISM: Homo sapiens
```

-continued

```
<220> FEATURE:
<223> OTHER INFORMATION: Transcription repressor d omain

<400> SEQUENCE: 3

Trp Arg Pro Trp
  1
```

GENE ORIGINATING IN HUMAN CHONDROCYTE

This application is a national stage application of PCT/JP98/03106, filed Jul. 10, 1998, which claims priority to JP 202227, filed Jul. 11, 1997.

TECHNICAL FIELD

This invention relates to a gene expressed specifically in differentiated chondrocytes originating in human (or human chondrocytes), a protein encoded by the gene, an antibody capable of binding to the protein, a method for culturing human chondrocytes in a differentiated state, and human chondrocytes that have been cultured by the method.

BACKGROUND ART

Searching for genes expressed specifically in chondrocytes in a differentiated state and analysis of the properties of the chondrocytes are not only important in analyzing the mechanism of differentiation and degeneration of cartilage, but also are indispensable for developing gene therapy for osteoarthritis and rheumatoid arthritis.

However, any method for monolayer culturing human chondrocytes in a differentiated state has not yet been established, although culture systems for rabbit or chicken chondrocytes in a differentiated state have been developed. (Kato et al. Proc. Natl. Acad. Sci. USA 85, 9552–9556 (1988); Oakes et al. J. Embryol. Exp. Morphol. 38, 239–263 (1977).) It is recognized that human chondrocytes maintain their differentiated phenotype in agarose gel (Benya P.D. and Shaffer J.D., Cell 30, 215–224 (1982)), but that they easily lose the differentiated phenotype in the monolayer culture which facilitates handling of cells. Accordingly, it is difficult to search for genes that are expressed specifically in human chondrocytes in a differentiated state thereof; there has not been provided any cell culture system useful in analyzing the properties of the chondrocytes in a differentiated state thereof.

DISCLOSURE OF INVENTION

A principle object of this invention is to establish a method of monolayer culture for human chondrocytes in a differentiated state and further to obtain a gene expressed specifically in the chondrocytes in a differentiated state thereof.

The present inventors found that chondrocytes could be cultured in a differentiated state by culturing the chondrocytes in the presence of a certain compound; and in addition, they searched for genes having a distinction in expression between differentiated chondrocytes and dedifferentiated chondrocytes and discovered those which were specifically expressed in the former. Thus, this invention has been accomplished.

Particularly, this invention provides a DNA encoding a protein defined in (a) or (b) as described below: the DNA may be referred to as "DNA of this (the) invention" hereinbelow.

(a) A protein comprising an amino acid sequence set forth in SEQ ID NO: 2.

(b) A protein comprising an amino acid sequence derived from the amino acid sequence set forth in SEQ ID NO: 2 by deletion or substitution of one or more amino acids therefrom, or by addition of one or more amino acids thereto and capable of binding to nucleotide sequence CANNTG and/or nucleotide sequence CACNAG upon formation of a dimer, wherein the amino acid sequence of a part of said protein corresponding to an amino acid sequence of from amino acid no. 51 to amino acid no. 108 in SEQ ID NO: 2 is provided with not less than 85% of homology to the amino acid sequence of from amino acid no. 51 to amino acid no. 108 in SEQ ID NO: 2. Preferably, DNA of this invention is a DNA defined in the following (c) or (d):

(c) A DNA comprising a nucleotide sequence of from nucleotide no. 207 to nucleotide no. 1442 of the nucleotide sequence set forth in SEQ ID NO: 1 or a complementary nucleotide sequence thereto.

(d) A DNA capable of hybridizing to the DNA defined in (c) under stringent conditions.

This invention also provides a protein encoded by DNA of the invention, as well as an antibody capable of binding to the protein.

Further, the invention provides a method for culturing human chondrocytes, which comprises monolayer culturing the chondrocytes in the presence of a membrane-permeable cAMP analog in an amount sufficient to cause the chondrocytes to maintain a differentiated state thereof as cartilage: the method may be referred to as "the culturing method of this (the) invention" hereinbelow. Preferably, the membrane-permeable cAMP analog is dibutyryl cAMP (which may be denoted "dbcAMP" hereinbelow).

Still further, the invention provides human chondrocytes that have been cultured by the culturing method of the invention and that possess the properties defined in the following (1)–(3):

(1) Exhibit a spherical shape and are abundant in extracellular matrix;

(2) Can be stained with toluidine blue satisfactorily ; and (3) DNA of the invention is expressed therein.

The DNA of this invention is believed to encode a novel transcription factor of the basic helix-loop-helix type (bHLH), and is predicted to play an important role such as the regulation of expression of various genes in the differentiation of cartilage. Therefore, a DNA of this invention, a protein encoded by the DNA, and an antibody capable of binding to the protein are useful in the analysis of mechanism of the differentiation and degeneration of cartilage, a well as in the development of gene therapy for osteoarthritis and rheumatoid arthritis.

According to the culturing method of this invention, chondrocytes can be monolayer cultured in a good differentiated state, which makes it easy to search for genes having a distinction in expression between chondrocytes in a differentiated state thereof and chondrocytes in a dedifferentiated state thereof: namely, to search for genes expressed specifically in chondrocytes in a differentiated state thereof. Also, an analysis of the properties of chondrocytes in a differentiated state thereof will be facilitated.

BREIF DESCRIPTION OF DRAWINGS

FIG. 1 shows a comparison between DEC1 and other bHLH factors in the bHLH region.

BEST MODE FOR CARRYING OUT THE INVENTION

Figure 2A:
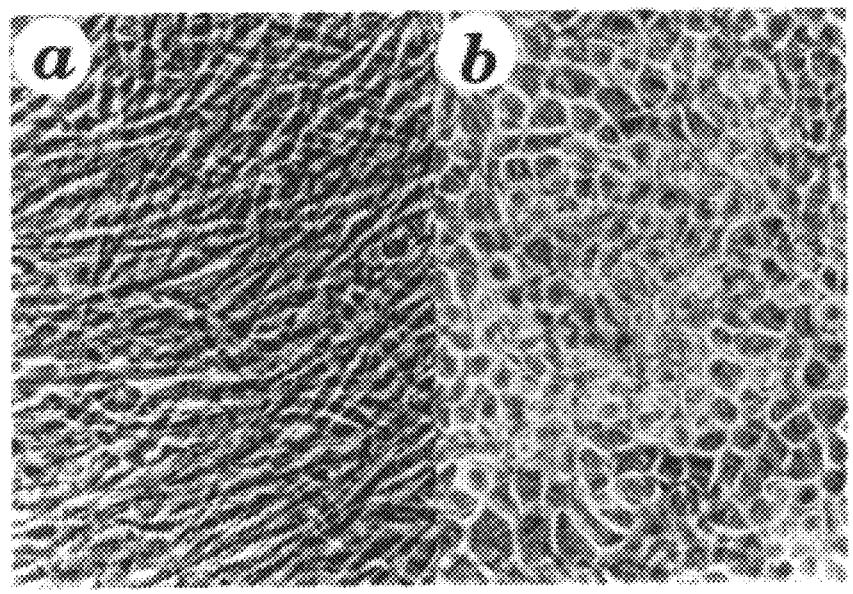
FIG. 2A is a photomicrograph showing the morphology of human chondrocytes in monolayer culture (a-no addition of dbcAMP, b-addition of dbcAMP).

Embodiments of this invention will be explained hereinbelow.

As will be later shown in the Examples, any genes expressed specifically in chondrocytes in a differentiated state were searched for; and as a result, the amino acid sequence set forth in SEQ ID NO: 2 has been revealed for the first time. As used in the present specification, the protein having this amino acid sequence may be referred to as "DEC1."

Through a homology search using a protein database, it was found that DEC1 has a basic helix-loop-helix (bHLH) region (amino acid nos. 51–108 in SEQ ID NO: 2). It is known that a bLHL protein forms a dimer and binds to E box (CANNTG).

Particularly, in this bHLH region, rat HES1 (47.5%), rat HES2 (42.6%), rat HES3 (40.3%), rat HES5 (37.7%), Drosophila Hairy (abbreviated as "hairy") (39.3%), and Enhancer of Split m7 (abbreviated as "E(spl)m7") (37.7%) showed high homology: numerical values in the parentheses represent homology levels. FIG. 1 shows corresponding bHLH regions of the respective proteins for comparison. The conserved residues are enclosed by the frames.

The HES family, hairy, and E(spl)m7 function as negative regulators which repress transcription by binding to N box (CACNAG). (Sasai et al. Genes & Dev. 6, 2620–2634 (1992); Ishibashi et al. Eur. J. Biochem. 215, 645–652 (1993); Akazawa et al. J. Biol. Chem. 267, 21879–21885 (1992); Ohsako et al. Genes & Dev. 8, 2743–2755 (1994); Dawson et al. Mol. Cell. Biol. 15, 6923–6931 (1995); Jan et al. Cell 75, 827–830 (1993).) They also have the Trp-Arg-Pro-Trp (WRPW) domain (SEQ ID NO: 3) at their C-terminus: the domain is believed to lead to suppression of a certain activator by a repressor (Dawson et al. Mol. Cell. Biol. 15, 6923–6931 (1995)). Although DEC1 resembles a bHLH factor, it does not have this WRPW domain. Thus, DEC1 is believed to be a novel transcription factor that modulates chondrogenesis. In view of the foregoing, it is thought that DEC1 is able to bind to E box, as well as to N box.

Accordingly, the DNA of this invention encompasses: a DNA that encodes a protein comprising the amino acid sequence set forth in SEQ ID NO: 2; and in addition, a protein comprising an amino acid sequence derived from the amino acid sequence set forth in SEQ ID NO: 2 by deletion or substitution of one or more amino acids therefrom, or by addition of one or more amino acids thereto and capable of binding to nucleotide sequence CANNTG and/or nucleotide sequence CACNAG (preferably, nucleotide sequence CANNTG) upon formation of a dimer, wherein the amino acid sequence of a part of said protein corresponding to an amino acid sequence of from amino acid no. 51 to amino acid no. 108 in SEQ ID NO: 2 is provided with not less than 85% (preferably, not less than 90%) of homology to the amino acid sequence of from amino acid no. 51 to amino acid no. 108 in SEQ ID NO: 2. Here, "N" in the above-described sequence represents A, G, C, or T. For an example of nucleotide sequence CANNTG, mentioned are CACGTG, CAGGTG, CAGTTG, and CACCTG. The expression, "encoding a protein," means that either one of complementary double strands has a nucleotide sequence encoding the protein when the DNA is double-stranded.

Substitution, deletion, or insertion of (an) amino acid residue(s) can be generated by introducing into a nucleotide sequence, variation such as the substitution, deletion, or insertion of nucleotide, according to a known method (e.g., site-specific mutation). Methods for determining the activity which allow the binding to nucleotide sequence CANNTG or CACNAG when the dimer is formed are known: for example, see Ohsako et al. Genes & Dev. 8, 2743–2755 (1994). One skilled in the art can readily select such substitution, deletion, or insertion of one or more amino acid residues that would not substantially impair this activity.

Concrete examples of DNA of this invention encompass DNAs defined in the following (c) and (d):

(c) A DNA comprising a nucleotide sequence of from nucleotide no. 207 to nucleotide no. 1442 of the nucleotide sequence set forth in SEQ ID NO: 1 or a complementary nucleotide sequence thereto.

(d) A DNA capable of hybridization to the DNA defined in (c) under stringent conditions.

Here, the "stringent conditions" means the conditions under which a so-called specific hybrid is formed, but any non-specific hybrid is not formed. These conditions may be difficult to be accurately expressed as numerical values; and for example, mentioned is a temperature in the range of from Tm to Tm minus 20° C. where the Tm is the one for a perfectly matched hybrid, such as that between highly homologous nucleic acids, or alternatively the conditions under which DNAs having homology of not less than 80% hybridize to each other, but nucleic acids having homology lower than that do not hybridize to each other.

The DNA of this invention is preferably one that encodes the amino acid set forth in SEQ ID NO: 2, and is more preferably the DNA of (c) described above.

As will be later shown in the Examples, one of the nucleotide sequences for DNA of the invention has been determined; therefore, it is possible to synthesize the DNA based on this sequence. The DNA can also be obtained from chromosomal DNAs by PCR or hybridization using oligonucleotides or probes that have been prepared based on this very nucleotide sequence. Alternatively, the DNA can further be obtained either by carrying out RT-PCR with cartilage mRNA or by screening a cDNA library, such as cartilage, with polynucleotides having a nucleotide sequence that encodes the whole or a part of DEC1 as probes.

The protein encoded by DNA of this invention is a protein defined in (e) or (f) described below: the protein may be referred to as "the protein(s) of this (the) invention" hereinbelow.

(e) A protein comprising an amino acid sequence set forth in SEQ ID NO: 2.

(f) A protein comprising an amino acid sequence derived from the amino acid sequence set forth in SEQ ID NO: 2 by deletion or substitution of one or more amino acids therefrom, or by addition of one or more amino acids thereto and capable of binding to nucleotide sequence CANNTG and/or nucleotide sequence CACNAG upon formation of a dimer, wherein the amino acid sequence of a part of said protein corresponding to an amino acid sequence of from amino acid no. 51 to amino acid no. 108 in SEQ ID NO: 2 is provided with not less than 85% of homology to the amino acid sequence of from amino acid no. 51 to amino acid no. 108 in SEQ ID NO: 2.

The protein of this invention can be produced by the following steps: a DNA of this invention is inserted into a known expression vector to construct a recombinant plasmid; transformed cells are obtained by introducing this recombinant plasmid thereto; the transformed cells are cultured in a suitable medium to allow a protein of the invention to form and accumulate in the culture; and said protein is harvested from the culture.

Host-vector systems ordinarily used to express exogenous proteins can be employed as cell and expression vectors. For example, mentioned are a combination of a prokaryotic cell such as *E. coli* and an expression vector adapted to the cell and a combination of a eukaryotic cell such as a mammalian cell and an expression vector adapted to the cell. Culture media and culturing conditions may appropriately be selected in accord with the cells to be employed.

The proteins of this invention may be expressed as fusion proteins with other proteins. Also, the proteins of the invention may be expressed in their full-length, or alternatively, portions thereof may be expressed as partial peptides.

Cultures, as used herein, are media and cells in the media. Harvesting proteins of this invention from the cultures can be carried out according to known protein purification methods which utilize, among others, the above-mentioned activity of proteins of the invention as an index.

Antibodies capable of binding to the proteins of this invention can be prepared according to standard methods using the proteins of the invention as antigens: the antibodies may be referred to as "antibody (ies) of this (the) invention." The antibodies of this invention may be monoclonal antibodies or polyclonal antibodies.

The protein of this invention may be used intact as an antigen; however, it is preferred that the protein be conjugated to keyhole lymphet hemocyanine, bovine serum albumin, egg white albumin, etc. and/or be combined with adjuvants for use as the antigen.

An animal to be immunized such as a mouse, rabbit, guinea pig, or sheep is immunized by administration of the antigen described above via percutaneous, intraperitoneal, or intravenous injections or the like. A polyclonal antibody can, for example, be obtained by collecting serum from the immunized animal.

A monoclonal antibody can, for example, be obtained in the following manner. After an animal to be immunized such as a mouse, rabbit, guinea pig, or sheep is immunized by administration of the antigen described above via percutaneous, intraperitoneal, or intravenous injections or the like, its spleen or lymph node is extracted. Cells taken from this are fused with myeloma cells, which are preferably derived from the same animal species as that of the immunized animal, to create a hybridoma. A cell strain is selected by repeating screening and cloning from the obtained hybridoma: the strain incessantly produces an antibody specific to the above-mentioned antigen. A monoclonal antibody is produced in a suitable medium by culturing the thus-selected cell strain in the medium; or alternatively, it is produced in an ascite fluid or the like by culturing the strain in vivo, such as mouse abdominal cavities.

Purification methods for the resulting polyclonal and monoclonal antibodies include salting out with ammonium sulfate, ion-exchange chromatography using a DEAE cellulose column or the like, affinity chromatography using a Protein A column, and immunoabsorption chromatography. The antibodies of this invention can be detected by immunoassays using the proteins of the invention or labeled antibodies.

The antibodies of this invention may be fragmented ones, so long as they retain antigen-binding sites (Fab). Specifically mentioned as the present fragmented antibody is a fragment containing Fab that can be obtained by digesting the present antibody with a protease such as papain which does not digest the antigen-binding site.

The antibodies of this invention may be labeled by being bound to labeling substances. The labeling substances are not particularly limited, so long as they can ordinarily be used in labeling of proteins; and mentioned are enzymes, isotopes, fluorescent substances, etc.

Next, the culturing method of this invention will be explained. The method of the invention is characterized in that it comprises monolayer culture of chondrocytes in the presence of a membrane-permeable cAMP analog in an amount sufficient to cause the chondrocytes to maintain a differentiated state thereof as cartilage.

Monolayer culture of chondrocytes can be carried out in a manner similar to the conventional monolayer culture of chondrocytes, except that it is to be done in the presence of the membrane-permeable cAMP analog. For example, the media that are used for culture include α-modified Eagle's medium containing fetal bovine serum, ascorbic acid, an antibiotic, etc. as appropriate.

The membrane-permeable cAMP analog is an analog of cAMP that has the ability to permeate the membrane without impairing its function as a so-called second messenger of CAMP; preferably, it is dibutyryl cAMP.

The quantity of the membrane-permeable cAMP analog present in a medium may be such that it is sufficient to cause the chondrocytes to maintain a differentiated state thereof as cartilage. For example, in the case of dibutyryl cAMP, it is preferably 0.3–0.5 mM.

As used in the present specification, the "differentiated state" means that the chondrocytes possess at least the properties described in the following (1) to (2):

(1) Exhibit a spherical shape and are abundant in extracellular matrix; and (2) Can be stained with toluidine blue satisfactorily.

The membrane-permeable cAMP analog in an amount sufficient to cause chondrocytes to maintain a differentiated state thereof as cartilage can also induce the differentiation of dedifferentiated chondrocytes.

Furthermore, this invention provides human chondrocytes that have been cultured by the culturing method of the invention and that possess the properties described in the following (1) to (3):

(1) Exhibit a spherical shape and are abundant in extracellular matrix;

(2) Can be stained with toluidine blue satisfactorily; and (3) DNA of this invention is expressed therein.

Since toluidine blue selectively stains sulfated proteoglycan, the chondrocytes of this invention synthesize the sulfated proteoglycan.

These chondrocytes express mRNAs for collagen of Type I and Type II as well as those for aggrecan.

EXAMPLES

This invention will be explained by way of examples hereinbelow.

EXAMPLE 1

Culture of Chondrocytes in Differentiated State

Epiphyseal cartilage of the femur knee joint of a human fetus that was naturally aborted about 25 weeks of pregnancy (obtained from Norman Bethune University of Medical Sciences, Department of Pathology) was obtained. Chondrocytes were isolated from this cartilage according to the same method as that described in Shimomura et al. Calcif.

Tissue Res. 19, 179–187 (1975), except that the finely cut cartilage was incubated in a α-modified Eagle's medium (α-MEM) containing 3 mg/ml collagenase (Type IA, Sigma) for 3 h. The cells were seeded at $1\times10^5$ cells per Type I collagen-coated dish and maintained in α-MEM (10 ml/dish) containing 10% fetal bovine serum, 50 μg/ml of ascorbic acid, 32 unit/ml of penicillin, and 40 μg/ml of streptomycin. Dibutyryl cAMP (dbcAMP) (1 mM) was added to the culture medium when the cells became sub-confluent. Cells were cultured over two days either in the presence or in the absence of dbcAMP. Then, while the cells were harvested, the morphological change of cells was examined. After fixing with ethanol, the cells were stained with toluidine blue.

The chondrocytes cultured in the presence of dbcAMP exhibited a spherical shape and were abundant in extracellular matrix, whereas the chondrocytes cultured in its absence were fibroblast-like and have a spindle shape, and were deficient in extracellular matrix. FIG. 2A shows a photomicrograph of the morphology of cells on the 6th day after addition of dbcAMP (a-no addition of dbcAMP, b-addition of dbcAMP).

Figure 2B:
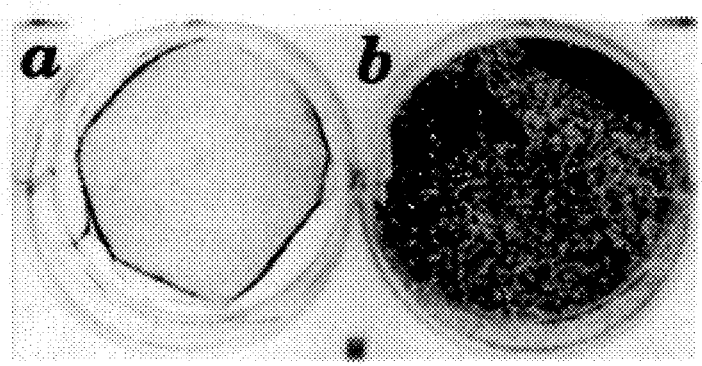
FIG. 2B is a photograph showing the morphology of human chondrocytes in monolayer culture (the morphology of an organism) that were stained with toluidine blue (a-no addition of dbcAMP, b-addition of dbcAMP).

In the staining with toluidine blue that should selectively stain sulfated proteoglycan, the chondrocytes cultured in the presence of dbcAMP were stained satisfactorily, whereas the chondrocytes cultured in its absence were hardly stained. FIG. 2B shows the results of staining with toluidine blue of cells on the 12th day after addition of dbcAMP (a: no addition of dbcAMP, b: addition of dbcAMP).

Expression of the mRNA for Type I and Type II collagen, and aggrecan which serve as differentiation markers, was investigated by RT-PCR. Expressions of the differentiation markers were compared in the presence of dbcAMP as well as in its absence; as a result, it was indicated that the differentiated state was maintained in the presence of dbcAMP.

Accordingly, it was recognized that the chondrocytes cultured in the presence of dbcAMP maintained a differentiated state thereof as cartilage (namely, the maintenance of a differentiated phenotype).

When dose-dependence of the above-noted effect by dbcAMP was studied, said effect increased in a dose-dependent manner, reaching its maximum at 0.3–0.5 mM.

It has been reported that bFGF and TGF-β stabilize or stimulate the expression of rabbit or chicken chondrocytes of the differentiated phenotype. Employing bFGF (0.4 ng/ml) and TGF-β (3 ng/ml), the chondrocytes were cultured similarly to above, but they did not maintain their differentiated phenotype in human chondrocytes.

EXAMPLE 2

Expression of Specific Genes in the Differentiated Chondrocytes

Total RNA was extracted from the chondrocytes cultured in the presence of dbcAMP and those cultured in the absence of dbcAMP (as described in Example 1) by the guanidinethiocyanate/cesium trifluoroacetate method. Poly (A)+RNA was concentrated using Oligotex-dT30 (Roche). The subtractive hybridization was used to select clones in which mRNA was observed that had been expressed in the differentiated chondrocytes (+dbcAMP) but not in the dedifferentiated chondrocytes (–dbcAMP). Using a PCR select cDNA subtraction kit (Clonetech), cDNA synthesized from the mRNA of the differentiated chondrocytes was allowed to hybridize with an excess amount of cDNA ofrom the mRNA of the dedifferentiated chondrocytes. The cDNA that did not hybridize, namely that was expressed in a differentiated state was amplified by suppression PCR according to the manufacturer's manual. The resulting PCR product was cloned into pGEM-T (Promega), a T tail vector, and the nucleotide sequence determination was carried out on about 120 clones. One clone (pSUB37) was selected for further analysis, and the corresponding protein product was named DEC1.

NcoI-PstI fragment from pSUB37 was used as a probe to study the expression of DEC1 mRNA in various human fetus tissues by Northern blot analysis. Consequently, DEC1 was expressed in the cartilage, spleen, intestine, and lung; and it was also expressed in the heart, liver, brain, and stomach, although in small amounts. The Northern blot analysis was conducted in the following manner. Total RNA samples (5 or 10 μg) were electrophoresed on a 1% agarose gel containing formaldehyde and were transferred to Highbond-N-membranes (Amersham). Total RNA samples of various human fetus tissues were provided by Dr. Li Yu at Norman Bethune University of Medical Sciences, which were intended for the study of tissue distribution. NcoI-PstI fragment from pSUB37 was labeled with [$^{32}$P]dCTP, and it was used as a hybridization probe. The membranes were washed with 2×SSC containing 0.5% SDS at 65° C. for 30 min. Biomax X-ray films were exposed to the washed membranes using sensitizing films at –70° C.

The full-length nucleotide sequence of DEC1 cDNA was determined in the following manner. A full-length cDNA of DEC1 was isolated by RACE (rapid amplification cDNA ends method) using a Marathon cDNA amplification kit (Clonetech). Specifically, a double-stranded cDNA was ligated to a Marathon cDNA adapter and subjected to suppression PCR. Reaction was carried out using an adapter primer and a gene-specific primer that had been designed for DEC 1 based on the nucleotide sequence of pSUB37. The amplified cDNA sample was separated on a 4% polyacrylamide gel, DNA of the main band was extracted from the gel, and it was subcloned into PGEM-T. Double-stranded DNA of the subcloned plasmid and a series of synthetic oligonucleotides were used as a sequence-determining template and as a specific primer, respectively. DNA sequence determination was carried out by the Sanger method using either a sequenase 7-deaza-dGTPDNA sequencing kit (Amersham) or an ABI PRIZM 310 autosequencer (Perkin-Elmer).

The nucleotide sequence of DEC1 cDNA thus determined and the amino acid sequence deduced therefrom are set forth in SEQ ID NO: 1. This amino acid sequence alone is also set forth in SEQ ID NO: 2. DEC1 cDNA has an open reading frame of 1236 bp. A 2922 bp length, excluding the poly A region, is well in accord with the size of mRNA (3.1 kb) that was obtained by the Northern blot analysis described above. Since there is a stop codon in the 5'-region which serves as an inframe, the first ATG is regarded as an initiation codon. The sequence around the first ATG coincides with a Kozak consensus sequence (GCCGCCA/GCCATGG). Thus, DEC1 comprises 412 amino acids and its calculated molecular weight is 45.5 kDa.

EXAMPLE 3

(1) Materials and Methods

Chondrocytes were isolated from the rib growth plate and resting cartilage of ribs of a male Japanese white rabbit (four-weeks old) according to the method as already reported in Shimomura et al. Calcif. Tissue Res. 19, 179–187 (1975).

These cells were seeded at $5\times10^5$ cells per 100 mm plastic culture dish and maintained in 10 ml of α-MEN supplemented with 10% FBS, 60 mg/ml of kanamycins, 250 ng/ml of amphotericin B, and 50 unit/ml of penicillin G at 37° C. in the air containing 5% $CO_2$. After cells reached confluent, the cells were washed with PBS, transferred to a fresh α-MEN (10 ml) containing no serum, and maintained for 48 h. From 1 to 24 h before the completion of incubation, 1 mM dbcAMP or $10^7$ M human recombinant PTH(1–84) was added to the medium.

Human embryonic pulmonary fibroblasts (MRC-5), human cervix uteri epithelial cells (Hela), human hepatoma cells (HepG2) and canine renal epithelial cells (MDCK) were obtained from the Gene Bank of The Institute of Physical and Chemical Research. Cells were cultured in modified Dalbeco Eagle's media (DMEM) supplemented with 10% FBS until they reached confluent. After the cultures had turned confluent, the cells were washed with PBS, transferred to fresh DMEM (10 ml) containing no serum, and maintained for 48 h. From 1 to 24 h before the completion of incubation, 1 mM dbcAMP was added to the media. Then, cells were harvested for RNA preparations.

(2) Northern Blot Analysis

Total RNAs were extracted from the cultured cells by the guanidine thiocyanate/cesium trifluoroacetate method. (Smale G. and Sasse J., Anal. Biochem. 203, 352–356 (1992).) The total RNA samples (8–20 μg) were electrophoresed on a 1% agarose gel containing formaldehyde and were transferred to NYTRAN membranes (Schleicher & Schuell, Japan). A 1.1 kb NcoI-PstI fragment from pSUB37 was labeled with [$^{32}$P]dCTP, and it was used as a hybridization probe. The membranes were washed with 0.2×SSC containing 0.5% SDS at 55° C. for 30 min. BioMax X-ray films (Eastman Kodak Co., Rochester, N.Y.) were exposed to the washed membranes using sensitizing screens at −70° C.

Figure 3:
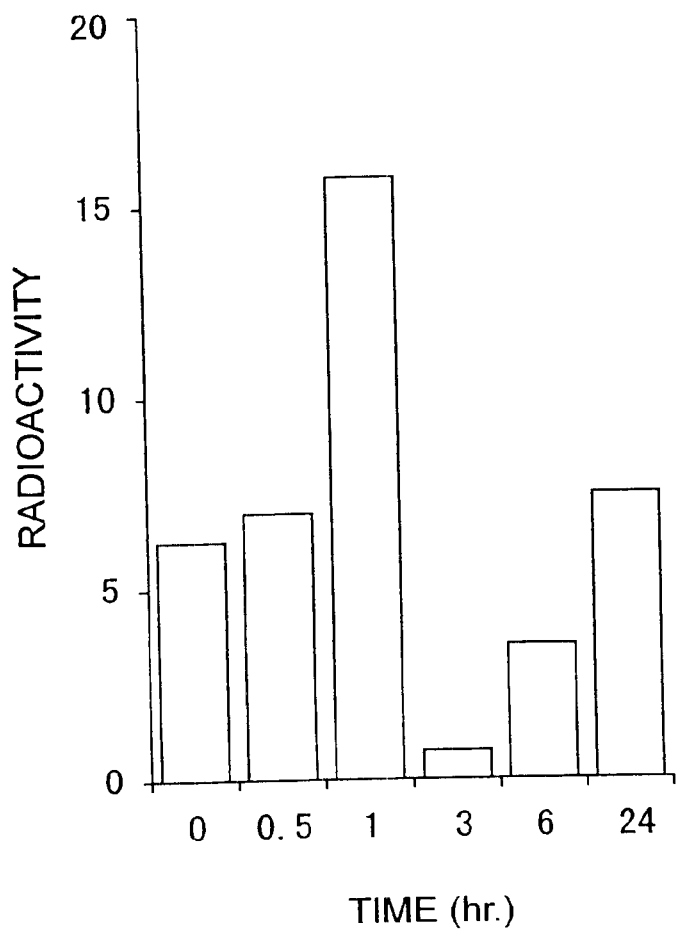
FIG. 3 is a graph showing that DEC1 mRNA was induced in a fibroblast strain, MRC5, originating in the human lung after addition of dbcAMP.

(3) Results (I) In human pulmonary fibroblast cell line MRC5, DEC1 mRNA was induced from 1 to 24 h after addition of dbcAMP (FIG. 3).

Figure 4:
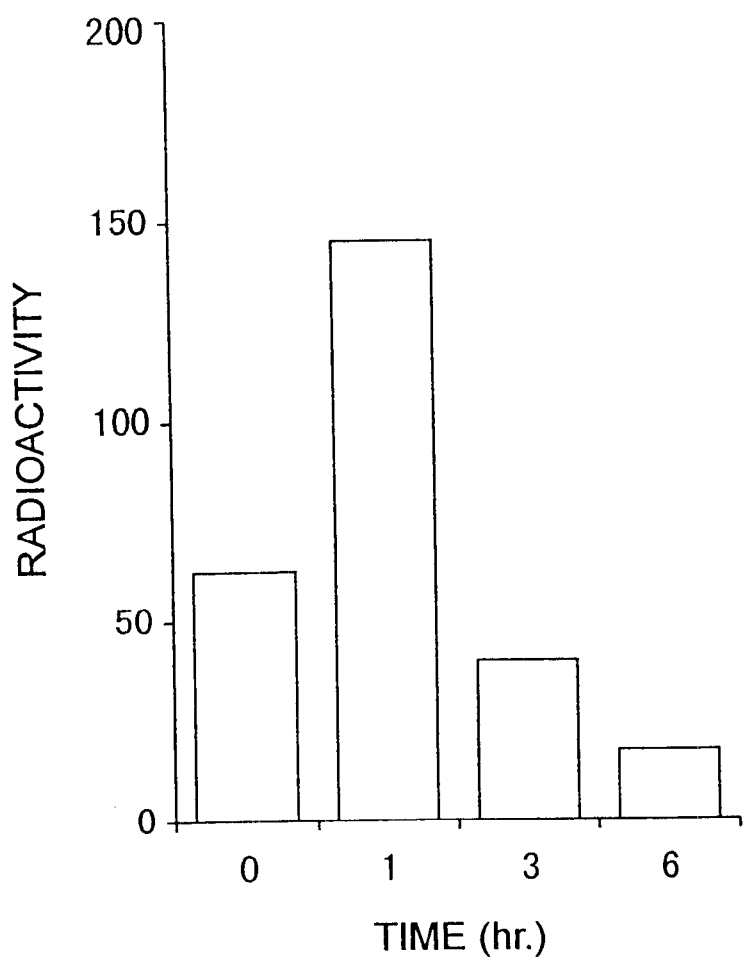
FIG. 4 is a graph showing that DEC1 mRNA was induced in Hela cells originating in human uterine cancer after addition of dbcAMP.

(II) In their cells originating in human uterine cancer, DEC1 mRNA was also induced within 1 h after addition of dbcAMP (FIG. 4).

Figure 5:
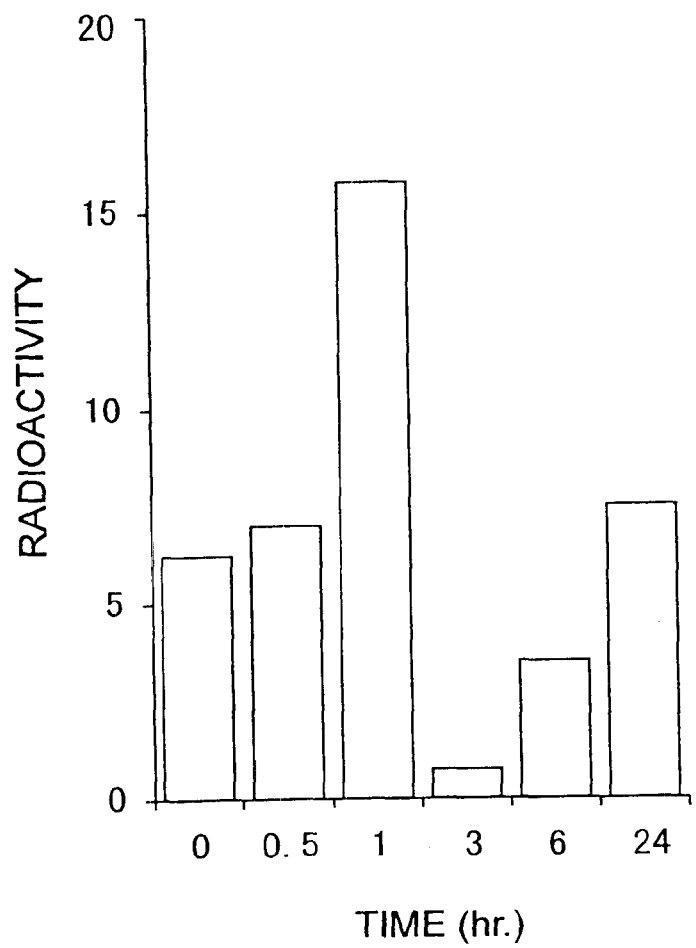
FIG. 5 is a graph showing that DEC mRNA was induced in rabbit chondrocytes after addition of PTH.

(III) In the rabbit chondrocytes, DEC1 mRNA was induced from 1 to 24 h after addition of PTH (FIG. 5).

Figure 6:
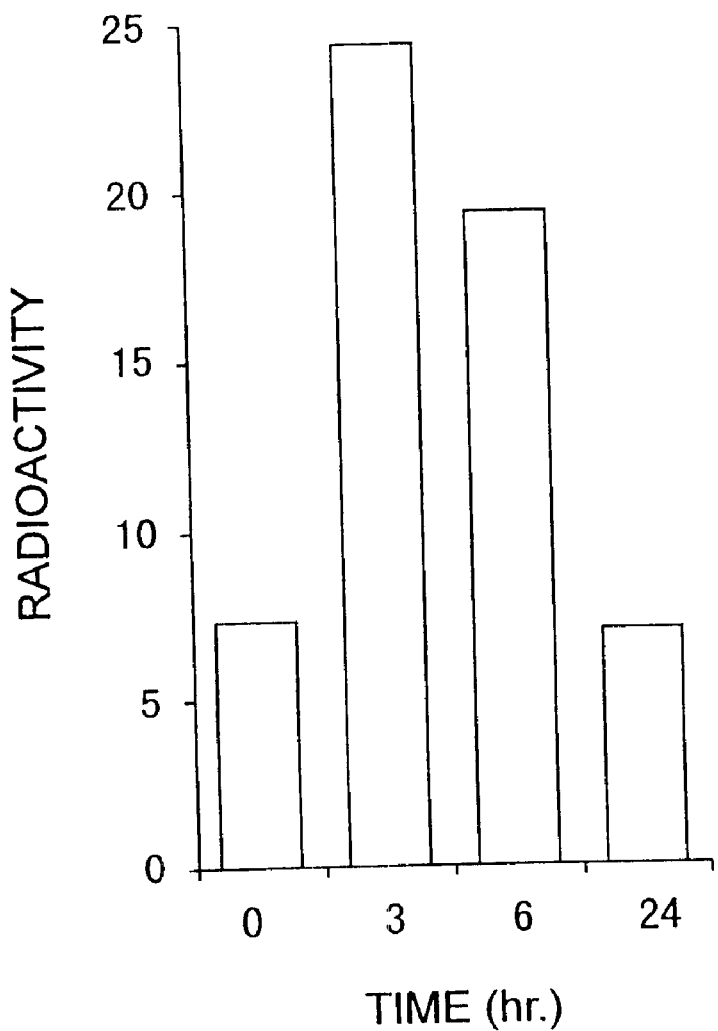
FIG. 6 is a graph showing that DEC1 mRNA was induced in a rabbit chondrocyte culture system after addition of dbcAMP.

(IV) In the rabbit chondrocyte culture system, it was also confirmed that DEC1 mRNA had been induced after addition of dbcAMP (FIG. 6)

(v) In the HepG2 cell strain originating in human hepatic cell line, no change in the level of DEC1 mRNA was observed between 1 to 6 h after addition of dbcAMP.

Figure 7:
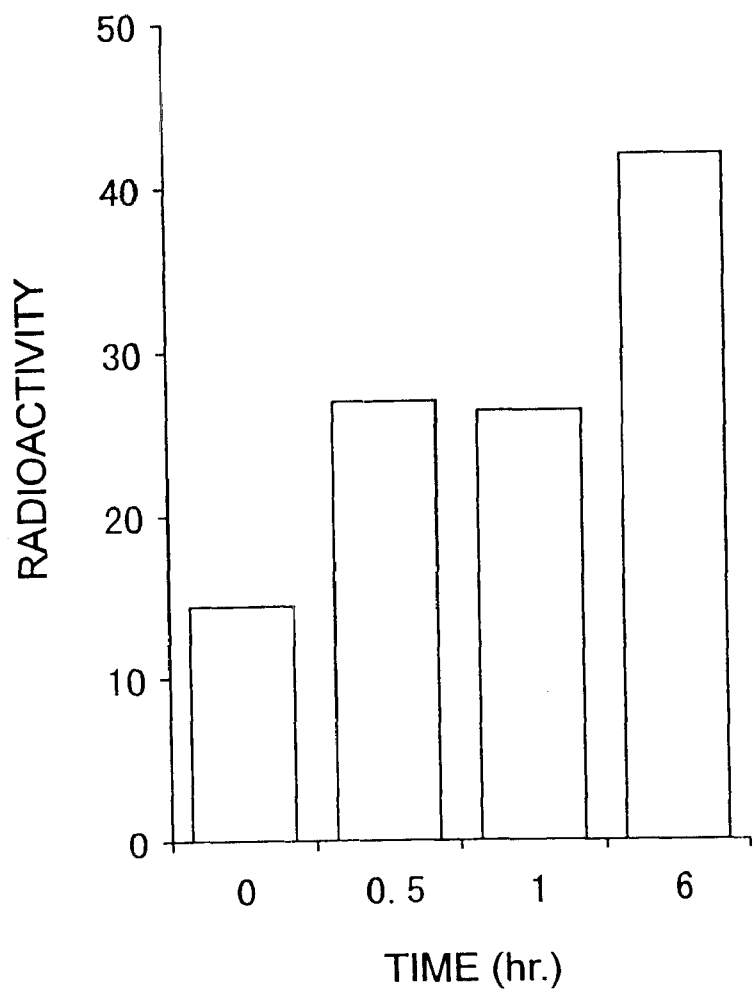
FIG. 7 is a graph showing that DEC1 mRNA was induced in a renal cell strain after addition of dbcAMP.

(VI) In the renal cell strain, the addition of dbcAMP also induced DEC1 mRNA (FIG. 7).

The above results have indicated that DEC1bHLH transcription factor is involved in the mechanism of action of PTH/PTHrp in chondrocytes. Furthermore, the DEC1bHLH transcription factor was induced in response to the cAMP within one hour in almost all the mesenchymal and epithelial cells tested. This has suggested that the present transcription factor almost universally participates in the gene expression of the cAMP signal system.

Industrial Applicability

As has been explained above, according to this invention there are provided a gene specifically expressed in differentiated human chrondrocytes, a method for culturing human chrondrocytes in a differentiated state, and human chrondrocytes that have been cultured by the method. These are important not only in the analysis of differentiation and degeneration of cartilage, but also in the development of gene therapy for osteoarthritis and rheumatoid arthritis. Moreover, they are believed to be useful in the treatment of diseases involving other cAMP systems, because cAMP induces DEC1 mRNA in a large number of cells other than the chrondrocytes.

What is claimed is:

1. An isolated DNA molecule encoding a protein comprising the amino acid sequence of SEQ ID NO: 2.

2. An isolated DNA molecule comprising nucleotides 207 to 1442 of SEQ ID NO: 1 or a nucleotide sequence complementary to nucleotides 207 to 1442 of SEQ ID NO: 1.

3. An isolated protein comprising the amino acid sequence of SEQ ID NO: 2.

* * * * *